United States Patent
Maruyama (10) Patent No.: US 9,031,854 B2
(45) Date of Patent: May 12, 2015

(54) ULTRASONIC DIAGNOSIS SUPPORT SYSTEM, ULTRASONIC IMAGING APPARATUS, AND ULTRASONIC DIAGNOSIS SUPPORT METHOD

(75) Inventor: Toshie Maruyama, Yaita (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1526 days.

(21) Appl. No.: 12/028,379

(22) Filed: Feb. 8, 2008

(65) Prior Publication Data

US 2008/0208048 A1 Aug. 28, 2008

(30) Foreign Application Priority Data

Feb. 27, 2007 (JP) ................. 2007-046619

(51) Int. Cl.
*G06Q 10/00* (2012.01)
*A61B 8/06* (2006.01)
*A61B 8/00* (2006.01)
*G06F 19/00* (2011.01)

(52) U.S. Cl.
CPC . *A61B 8/06* (2013.01); *A61B 8/463* (2013.01); *A61B 8/467* (2013.01); *G06F 19/321* (2013.01); *G06F 19/363* (2013.01)

(58) Field of Classification Search
CPC ..... G06T 7/0012; A61B 8/0825; A61B 6/463
See application file for complete search history.

(56) References Cited

U.S. PATENT DOCUMENTS

| | | | |
|---|---|---|---|
| 6,032,678 A * | 3/2000 | Rottem | 600/437 |
| 6,149,585 A * | 11/2000 | Gray | 600/300 |
| 6,394,952 B1 * | 5/2002 | Anderson et al. | 600/300 |
| 6,466,687 B1 * | 10/2002 | Uppaluri et al. | 382/128 |
| 6,823,203 B2 * | 11/2004 | Jordan | 600/407 |
| 6,925,200 B2 * | 8/2005 | Wood et al. | 382/132 |
| 6,979,294 B1 * | 12/2005 | Selzer et al. | 600/450 |
| 7,072,501 B2 * | 7/2006 | Wood et al. | 382/132 |
| 7,187,790 B2 * | 3/2007 | Sabol et al. | 382/128 |
| 7,556,602 B2 * | 7/2009 | Wang et al. | 600/437 |
| 2002/0032583 A1 * | 3/2002 | Joao | 705/2 |
| 2002/0052562 A1 * | 5/2002 | Lipman | 600/557 |
| 2002/0070970 A1 * | 6/2002 | Wood et al. | 345/766 |
| 2002/0198454 A1 * | 12/2002 | Seward et al. | 600/437 |
| 2003/0007598 A1 * | 1/2003 | Wang et al. | 378/37 |
| 2003/0095697 A1 * | 5/2003 | Wood et al. | 382/131 |

(Continued)

FOREIGN PATENT DOCUMENTS

JP 2006-305337 11/2006

*Primary Examiner* — Nicholas Evoy (74) *Attorney, Agent, or Firm* — Oblon, McClelland, Maier & Neustadt, L.L.P.

(57) ABSTRACT

The controller causes a display to display body marks representing the body parts of a subject to be imaged. Furthermore, the controller causes the display to display subjective symptom marks corresponding to the subjective symptoms of a subject to be examined in a location within a body mark that has been designated by an examiner. The examiner conducts ultrasonic imaging by applying an ultrasonic probe to a subject to be examined while checking the location of the subjective symptom marks. The controller links a tomographic image obtained from the imaging to the subjective symptoms and causes a storage to store the same. In the medical examination, the controller causes the display to display the tomographic image and further causes the display to display the subjective symptom marks representing the subjective symptoms linked to the tomographic image.

13 Claims, 5 Drawing Sheets

(56) References Cited

U.S. PATENT DOCUMENTS

| | | | |
|---|---|---|---|
| 2003/0103665 A1* | 6/2003 | Uppaluri et al. | 382/131 |
| 2003/0212327 A1* | 11/2003 | Wang et al. | 600/437 |
| 2004/0116812 A1* | 6/2004 | Selzer et al. | 600/467 |
| 2004/0116813 A1* | 6/2004 | Selzer et al. | 600/467 |
| 2004/0122702 A1* | 6/2004 | Sabol et al. | 705/2 |
| 2004/0122706 A1* | 6/2004 | Walker et al. | 705/2 |
| 2004/0122707 A1* | 6/2004 | Sabol et al. | 705/2 |
| 2004/0122708 A1* | 6/2004 | Avinash et al. | 705/2 |
| 2004/0122787 A1* | 6/2004 | Avinash et al. | 706/50 |
| 2004/0138559 A1* | 7/2004 | Cheng et al. | 600/437 |
| 2005/0152587 A1* | 7/2005 | Sirohey et al. | 382/128 |
| 2005/0256392 A1* | 11/2005 | Matory et al. | 600/407 |
| 2005/0267338 A1* | 12/2005 | Lipman | 600/300 |
| 2006/0008923 A1* | 1/2006 | Anderson et al. | 436/518 |
| 2006/0018834 A1* | 1/2006 | Weisskoff et al. | 424/9.2 |
| 2006/0064017 A1* | 3/2006 | Krishnan et al. | 600/450 |
| 2006/0064396 A1* | 3/2006 | Wei et al. | 707/1 |
| 2006/0136259 A1* | 6/2006 | Weiner et al. | 705/2 |
| 2006/0167529 A1* | 7/2006 | Schecter | 607/59 |
| 2006/0173708 A1* | 8/2006 | Vining et al. | 705/2 |
| 2006/0241431 A1 | 10/2006 | Kamiyama | |
| 2006/0251301 A1* | 11/2006 | McNamara et al. | 382/128 |
| 2007/0003124 A1* | 1/2007 | Wood et al. | 382/131 |
| 2007/0106751 A1* | 5/2007 | Moore | 709/217 |
| 2007/0116037 A1* | 5/2007 | Moore | 370/462 |
| 2007/0118399 A1* | 5/2007 | Avinash et al. | 705/2 |
| 2007/0168461 A1* | 7/2007 | Moore | 709/217 |
| 2007/0179811 A1* | 8/2007 | Reiner | 705/2 |
| 2007/0192134 A1* | 8/2007 | Littenberg et al. | 705/2 |
| 2008/0040151 A1* | 2/2008 | Moore | 705/2 |
| 2008/0059249 A1* | 3/2008 | Joao | 705/3 |
| 2008/0059250 A1* | 3/2008 | Joao | 705/3 |
| 2013/0111387 A1* | 5/2013 | Li et al. | 715/771 |

* cited by examiner

ULTRASONIC DIAGNOSIS SUPPORT SYSTEM, ULTRASONIC IMAGING APPARATUS, AND ULTRASONIC DIAGNOSIS SUPPORT METHOD

BACKGROUND OF THE INVENTION

1. Field of the Invention

The present invention relates to an ultrasonic diagnosis support system, an ultrasonic imaging apparatus, and an ultrasonic diagnosis support method for supporting diagnosis using ultrasonic images.

2. Description of the Related Art

The ultrasonic imaging apparatus comprises an ultrasonic probe comprising a plurality of ultrasonic transducers. The ultrasonic imaging apparatus transmits ultrasonic waves to a body to be examined through the ultrasonic probe and receives reflected waves from the body to be examined through the ultrasonic probe to generate ultrasonic image data (such as tomographic image data of a subject to be imaged) based on the reflected waves.

The ultrasonic images obtained by the ultrasonic imaging apparatus are used for medical examinations conducted by a medical examiner such as a doctor. For example, an ultrasonic imaging apparatus can be used for checking mammary glands (e.g., Japanese Unexamined Patent Application Publication 2006-305337). Herein, a case of conducting a mammary gland check using an ultrasonic imaging apparatus is described. First, the examiner conducts an interview with a subject to be examined (a person) regarding their subjective symptoms (e.g., presence or absence of lumps in the breasts, tension, pain, etc.). Then, the examiner images the breasts of the subject to be examined with an ultrasonic imaging apparatus to obtain tomographic image data. Areas with subjective symptoms that have been declared by the subject being examined are examined carefully by imaging from a plurality of directions. The examiner then saves any image data of areas determined to require a medical examination by a medical examiner such as a doctor, or the examiner simply outputs the image. Later, an examiner (doctor) can conduct a medical examination based on the images that have been saved or output and contact the subject being examined regarding the results of the medical examination.

As described, a medical checkup using an ultrasonic imaging apparatus is conducted through an interview by an examiner, imaging with ultrasonic waves, and a medical examination by a medical examiner (doctor). Furthermore, checkups of mammary glands using an ultrasonic imaging apparatus are conducted through group checkups. In this group checkup, the examiner conducts an interview with a plurality of subjects to be examined one after another and conducts imaging with ultrasonic waves.

However, when a plurality of subjective symptoms is declared by a subject being examined, the examiner must distinguish each subjective symptoms separately to conduct examinations. Therefore, the workload of the examiner increases and there is a risk that details regarding subjective symptoms or declared areas are mistaken, or that the examiner forgets to examine areas requiring an examination.

Furthermore, if the examiner and the medical examiner (doctor) are not the same subject, the relationship between the subjective symptoms declared by the subject to be examined and the image obtained by the examiner may be unclear to the medical examiner. Thus, there is a risk that the image may be underutilized, when a medical examiner examines a subject to be examined.

Moreover, there are cases in which areas containing subjective symptoms that have been declared by a subject to be examined are not imaged by an examiner. In this case, because an image representing the area with the subjective symptom does not exist, the medical examiner is not able to examine the area declared to have subjective symptoms through an image. Even if the examiner and the medical examiner are the same subject, the same problems as above have occurred when the medical examiner examines a subject to be examined after a few days.

SUMMARY OF THE INVENTION

The purpose of the present invention is to provide an ultrasonic diagnosis support system, an ultrasonic imaging apparatus, and an ultrasonic diagnosis support method for supporting an examiner so that imaging is possible without missing any body part of a subject to be examined. Furthermore, the purpose is to provide an ultrasonic diagnosis support system, an ultrasonic imaging apparatus, and an ultrasonic diagnosis support method for supporting a medical examiner so that the medical examiner is able to conduct an examination by taking medical questionnaire information of a subject to be examined into consideration when conducting a medical examination based on ultrasonic images.

A first aspect of the present invention is an ultrasonic diagnosis support system comprising: a receiver configured to receive medical questionnaire information related to a subject to be examined subject to medical examination; and a controller configured to designate a location that is regarding said received medical questionnaire information and is located in a body part of said subject to be examined subject to ultrasonic imaging, and to cause a display to display said received medical questionnaire information and the location information indicating said designated location.

According to the first aspect, when examining a subject to be examined using ultrasonic waves, the examination may be conducted while visually checking the medical questionnaire information by displaying the medical questionnaire information obtained from the subject to be examined and the location information related to the medical questionnaire information. It therefore becomes possible to image any body part of the subject to be examined without missing.

A second aspect of the present invention is based on the first aspect of the ultrasonic diagnosis support system. The second aspect of the ultrasonic diagnosis support system further comprises: an image-generator configured to transmit ultrasonic waves to said subject to be examined and to generate ultrasonic image data based on reflected waves from said subject to be examined; and an image-data-storage, wherein said controller is configured to link said medical questionnaire information as well as said location information to said generated ultrasonic image data and is configured to cause said image-data-storage to store the same.

According to the second aspect, when conducting a medical examination based on an ultrasonic image, it becomes possible for a medial examiner to conduct a medical examination while collating the medial questionnaire information of a subject to be examined and an ultrasonic image by linking the medical questionnaire information to the ultrasonic image data obtained from imaging with ultrasonic waves and by storing the same.

A third aspect of the present invention is based on the first aspect of the ultrasonic diagnosis support system. The third aspect of the ultrasonic diagnosis support system further comprises: a mark-storage configured to preliminarily store subjective symptom marks corresponding to the subjective symptoms of said subject to be examined and body marks representing body parts of said subject to be examined, wherein said receiver is configured to receive said medical questionnaire information including the subjective symptoms of said subject to be examined, and said controller is configured to execute: receiving designation of a body part subjected to ultrasonic imaging, acquiring the body mark representing said designated body part from said mark-storage; causing said display to display said body mark; receiving subjective symptom marks corresponding to the subjective symptoms included in said received medical questionnaire information from said mark-storage, receiving designation of the location within said body mark; and causing said display to display said acquired subjective symptom marks in said designated location within said body mark in an overlapping manner.

According to the third aspect, when examining a subject to be examined with ultrasonic waves, it is possible to conduct an examination while visually checking the subjective symptoms that have been declared by the subject to be examined using subjective symptom marks by displaying a subjective symptom mark corresponding to each subjective symptom that has been obtained from the subject to be examined on a body mark representing a body part to be subjected to ultrasonic imaging. It thereby becomes possible to image any body part with a subjective symptom of the subject to be examined without missing.

A fourth aspect of the present invention is based on the third aspect of the ultrasonic diagnosis support system. The fourth aspect of the ultrasonic diagnosis support system further comprises: an image-generator configured to transmit ultrasonic waves to said subject to be examined, and to generate ultrasonic image data based on said reflected waves from the subject to be examined, and an image-data-storage, wherein said controller is configured to link said medical questionnaire information as well as the location information indicating the location of said subjective symptom mark in said body mark to said generated ultrasonic image data and to cause said image-data-storage to store the same.

According to the fourth aspect, when conducting a medical examination based on an ultrasonic image, it becomes possible for a medial examiner to conduct a medical examination while collating a subjective symptom of a subject to be examined and an ultrasonic image by linking the medical questionnaire information to the ultrasonic image data obtained from imaging with ultrasonic waves and by storing the same.

A fifth aspect of the present invention is an ultrasonic imaging apparatus comprising: a mark-storage configured to preliminarily store subjective symptom marks corresponding to the subjective symptoms of a subject to be examined and body marks representing the body parts of said subject to be examined, an image-generator configured to transmit ultrasonic waves to said subject to be examined, and to generate ultrasonic image data based on reflected waves from said subject to be examined, a receiver configured to receive medical questionnaire information including the subjective symptoms of said subject to be examined, a controller configured to execute: receiving designation of a body part subjected to ultrasonic imaging; acquiring the body mark representing said designated part from said mark-storage; causing said display to display said body mark; acquiring subjective symptom marks corresponding to the subjective symptoms included in said received medical questionnaire information from said mark-storage; receiving designation of a location within said body mark; and causing said display to display said acquired subjective symptom marks in an overlapping manner with said designated location within said body mark; and an image-data-storage configured to store said medical questionnaire information and location information indicating the location of said subjective symptom marks in said body mark by linking to said generated ultrasonic image data.

A sixth aspect of the present invention is an ultrasonic diagnosis support method, comprising: entering medial questionnaire information related to a subject to be examined subject to medical examination; entering a location related to said received medical questionnaire information, the location being a body part of said subject to be examined subject to ultrasonic imaging; and displaying said received medical questionnaire information as well as the location information indicating said received location.

DETAILED DESCRIPTION OF THE EMBODIMENTS (Constitution)

Figure 1:
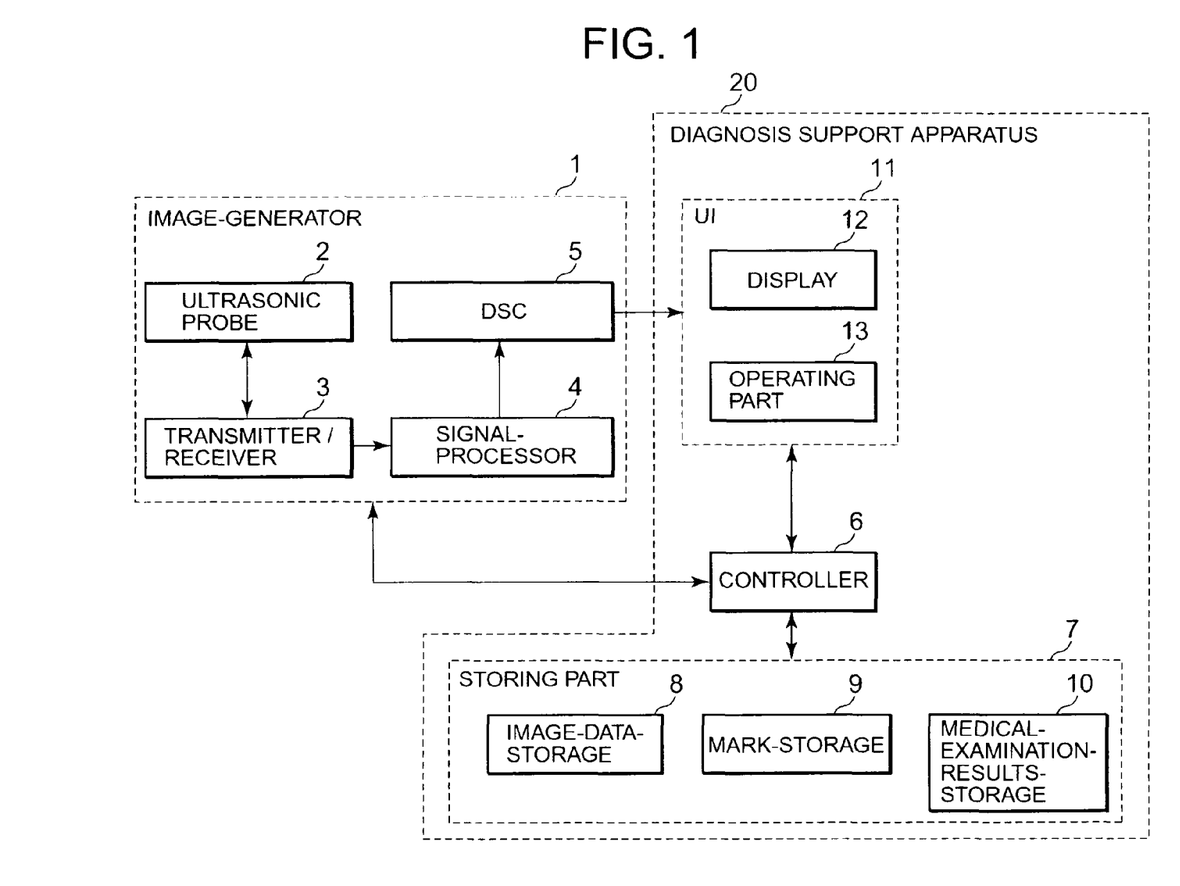
FIG. 1 is a block diagram showing an ultrasonic diagnosis support system related to an embodiment of the present invention.

An ultrasonic diagnosis support system related to the embodiment of the present invention is described referring to FIG. 1. FIG. 1 is a block diagram showing the ultrasonic diagnosis support system related to the embodiment of the present invention.

The ultrasonic diagnosis support system related to this embodiment is comprised by an image-generator 1, a controller 6, a storage 7, and a user interface (UI) 11. The controller 6, the storage 7, and the user interface (UI) 11 embody a diagnosis support apparatus 20. In the present invention, the ultrasonic diagnosis support system may also be embodied solely of the diagnosis support apparatus 20, and also the image-generator 1 and the diagnosis support apparatus 20 may embody the ultrasonic imaging apparatus.

The image-generator 1 transmits ultrasonic waves to a body to be examined and generates ultrasonic image data such as tomographic image data based on reflected waves from the body to be examined. The ultrasonic image data generated in the image-generator 1 is output to a display 12 and an ultrasonic image based on the ultrasonic image data is displayed in the display 12. The image-generator 1 comprises an ultrasonic probe 2, a transmitter/receiver 3, a signal-processor 4, and a DSC 5.

For the ultrasonic probe 2, a single-dimensional array probe in which a plurality of ultrasonic transducers are arranged in a row in the scanning direction (1D array probe) or a two-dimensional array probe in which a plurality of ultrasonic transducers are arranged two-dimensionally (2D array probe) is used. The transmitter/receiver 3 comprises a transmitter and a receiver. The transmitter is connected to each of the ultrasonic transducers of the ultrasonic probe 2. The transmitter performs a transmission beam focus by applying a delay when transmitting ultrasonic waves. The transmitter then supplies an electrical signal to each of the ultrasonic transducers to transmit ultrasonic waves that have been subjected to a beam form (transmission beam form) at a prescribed focal point. The receiver is connected to each of the ultrasonic transducers of the ultrasonic probe 2. By the receiver, an echo signal whose wave has been received by each of the ultrasonic transducers is amplified, and after an A/D conversion, the delay time required to determine the receiving directionality is given and added. Due to the addition, reflected waves from the direction according to the receiving directionality are fortified.

The signal-processor 4 comprises a B-mode processor, a Doppler-mode processor, and a CFM-processor. The data that has been output from the transmitter/receiver 3 undergoes a prescribed process in one of the processors. The B-mode processor conducts a Band Pass Filter process to the signal that has been output from the transmitter/receiver 3, and thereafter, detects the envelope curve of the output signal. The B-mode processor conducts imaging of the amplitude information of the echo with respect to the detected data through compression processing by logarithm conversion. The Doppler-mode processor generates blood flow information by employing a continuous Doppler method (CW Doppler method) or a pulse Doppler method (PW Doppler method). The CFM-processor conducts imaging of the moving blood flow information and generates colored ultrasonic raster data. The DSC5 (Digital Scan Converter) converts the data output from the signal-processor 4 to image data represented by a vertically crossing coordinate in order to obtain an image represented by a vertically crossing coordinate system (scan conversion processing). For example, DSC5 generates tomographic image data as two-dimensional information based on the output from the B-mode processor.

The ultrasonic image data such as tomographic image data that has been output from the DSC5 is output to the display 12 and an ultrasonic image based on the ultrasonic image data is displayed in the display 12.

The storage 7 comprises an image-data-storage 8, a mark-storage 9, and a medical-examination-results-storage 10. Specifically, the storage 7 is embodied by a storing device such as a hard disk.

The image-data-storage 8 stores ultrasonic image data such as tomographic image data generated in the image-generator 1. For example, the controller 6 attaches identification information such as patient ID to the tomographic image data in order to identify the subject to be examined and stores the tomographic image data attached with the identification information in the image-data-storage 8. The identification information such as a patient's ID are entered from an operating part 13 by an operator (examiner).

The mark-storage 9 stores subjective symptom marks representing subjective symptoms declared by the subject to be examined. The subjective symptom marks are different for each symptom. A plurality of subjective symptom marks are stored in the mark-storage 9. The mark-storage 9 also stores body marks representing the subject body part to undergo ultrasonic imaging.

Figure 2:
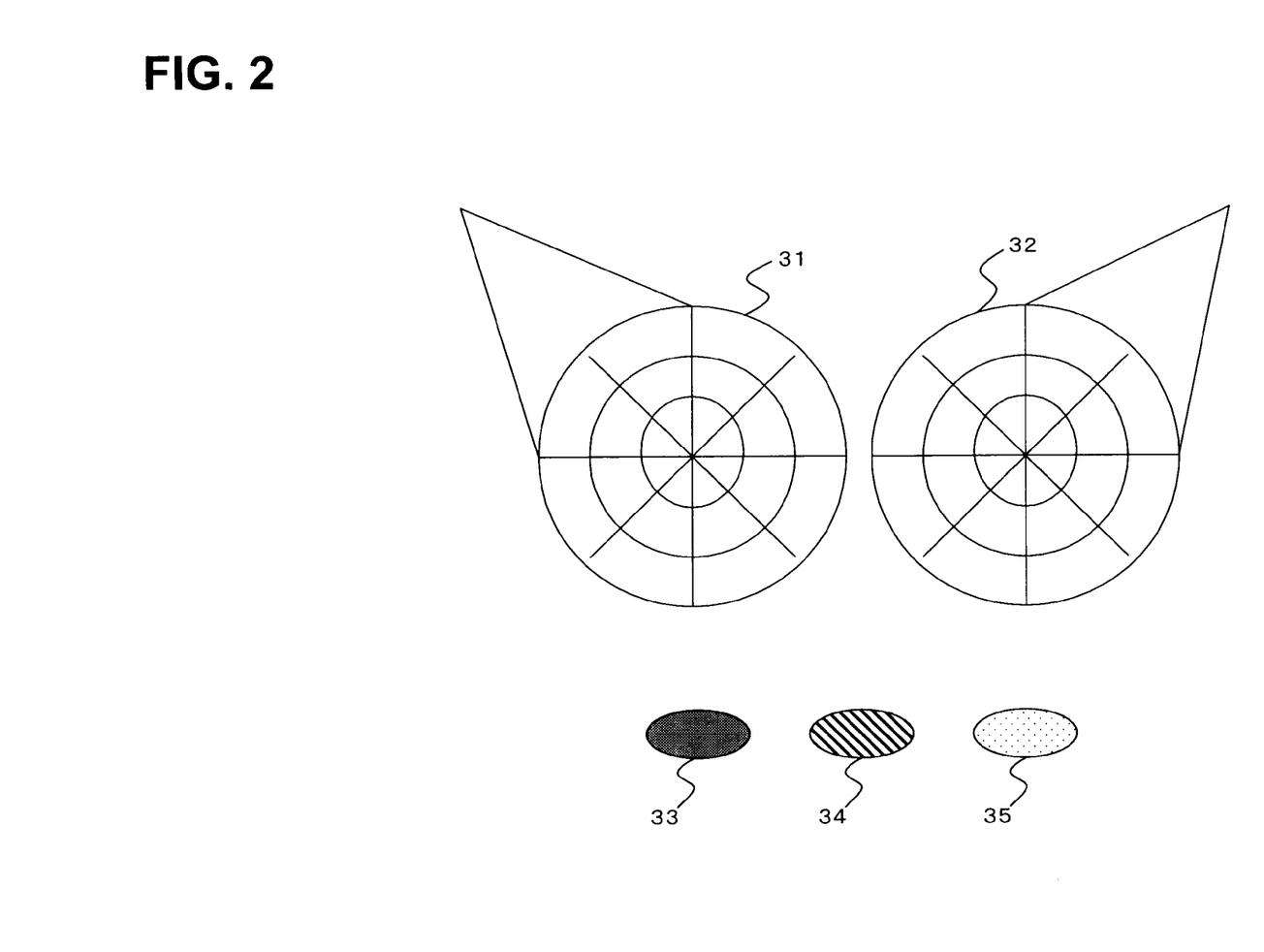
FIG. 2 illustrates a body mark and a subjective symptom mark representing a subjective symptom that is declared by a subject to be examined.

Herein, an example of subjective symptom marks and body marks is explained referring to FIG. 2. FIG. 2 illustrates body marks and subjective symptom marks representing subjective symptoms declared by a subject to be examined. In this embodiment, a case of imaging a breast is described as an example of a body part to be diagnosed.

Body marks 31, 32 are schematized marks of the shape of a breast. For example, the body mark 31 is a schematized mark of a breast on the right side of the subject to be examined. The body mark 32 is a schematized mark of a breast on the left side thereof. Furthermore, subjective symptom marks 33, 34, 35 are marks in which different colors or patterns have been implemented for each. The operator is thus able to distinguish each subjective symptom in accordance with the color or the pattern of the mark. For example, the subjective symptom mark 33 is a mark indicating a "lump", and the subjective symptom mark 34 is a mark indicating "pain". The subjective symptom mark 35 is a mark indicating "tension". As described, different subjective symptom marks 33, 34, 35 are prepared for each subjective symptom declared by the subject to be examined and are stored preliminarily in the mark-storage 9. To note, in the example shown in FIG. 2, three subjective symptom marks are being shown. These are merely examples of subjective symptom marks, and a plurality of subjective symptom marks are to be stored preliminarily in the mark-storage 9 in accordance with the declared subjective symptoms.

The controller 6 reads out a body mark that has been designated by the operator using the operating part 13 from the mark-storage 9 and causes the display 12 to display the body mark. For example, in case of examining a breast of the right side of the subject to be examined, the controller 6 causes the display 12 to display the body mark 31. Moreover, the controller 9 receives subjective symptoms that have been entered by the operator (examiner) with the use of the operating part 13, reads out subjective symptom marks corresponding to the received subjective symptoms from the mark-storage 9, and causes the display 12 to display the subjective symptom marks.

For example, the controller 6 creates a table listing a plurality of body marks that have been stored in the mark-storage 9 and causes the display 12 to display the table list. Furthermore, the controller 6 creates a table listing a plurality of subjective symptom marks that have been stored in the mark-storage 9 and causes the display 12 to display the table list. The operator (examiner) uses the operating part 13 to select a body mark representing a body part of a subject to be imaged from the list of body marks by referring to the table list. Upon receiving the selection from the operating part 13, the controller 6 causes the display 12 to display the selected body mark.

The operator (examiner) then conducts an interview with the subject to be examined to listen and determine the subjective symptoms from the subject to be examined. The operator (examiner) then selects subjective symptom marks representing the subjective symptoms that have been declared by the subject to be examined from the list of subjective symptom marks by using the operating part 13 and referring to the table list. Furthermore, the operator uses the operating part 13 to designate locations through body marks, which are equivalent to the areas that have been declared by the subject to be examined. The controller 6 receives the designated locations through the body marks from the operating part 13 and instructs to display the subjective symptom marks selected by the operator in the designated locations.

Figure 3:
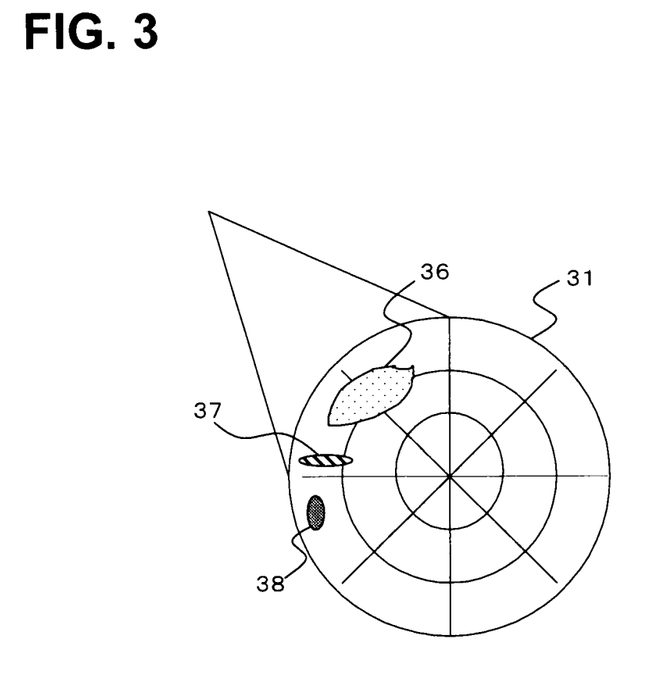
FIG. 3 illustrates a setting example of a mark representing a subjective symptom with respect to a body mark.

Herein, a setting example of subjective symptom marks on a body mark is explained referring to FIG. 3. FIG. 3 illustrates a setting example of subjective symptom marks representing subjective symptoms onto a body mark.

The operator (examiner) selects subjective symptom marks corresponding to the subjective symptoms obtained through an interview from the subject to be examined. Furthermore, the operator designates location using the body mark 31, which is equivalent to the area with a subjective symptom declared by the subject to be examined. For example, in a case when a subject to be examined has complained of a "lump", "pain", or "tension" as shown in FIG. 3, the operator selects a subjective symptom mark 36 meaning "lump", a subjective symptom mark 37 meaning "pain", and a subjective symptom mark 38 meaning "tension". Moreover, the operator uses the operating part 13 to designate locations through body mark 31, which is equivalent to the areas with the subjective symptoms declared by the subject to be examined. The controller 6 instructs to display the subjective symptom marks 36, 37, 38 selected by the operator with the use of the operating part 13 in the locations on the body mark 31, which has been designated by the operator. Moreover, it is possible to change the size or the shape of the subjective symptom marks. Once the size or the shape of a subjective symptom mark is designated by the operator with the use of the operating part 13, the controller 6 changes and instructs to display the subjective symptom mark into the size or the shape according to the designation.

Then, when the subjective symptom marks 36, 37, 38 are being displayed in an overlapping manner on the body mark 31, the operator (examiner) applies the ultrasonic probe 2 to the areas of the subject to be examined that are equivalent to the locations where the subjective symptom marks 36, 37, 38 have been set while checking the locations of the subjective symptom marks 36, 37, 38 that have been set on the body mark 31. In that state, the image-generator 1 scans the body to be examined with ultrasonic waves and generates ultrasonic image data such as tomographic image data.

As described, by displaying the subjective symptom mark 36 on the body mark 31 in an overlapping manner, the examiner is able to conduct imaging with ultrasonic waves while visually checking the area with a subjective symptom that has been declared by the subject to be examined. It thus becomes possible to conduct imaging without missing any body part with a subjective symptom declared by the subject to be examined. For example, even in a case where a subject to be examined declares a plurality of subjective symptoms to the examiner, by displaying the subjective symptom marks 36, 37, 38 on the body mark 31 in an overlapping manner, it becomes possible to conduct an examination while checking the declared areas with the subjective symptoms or the state thereof. Furthermore, forgetting to examine an area requiring an examination can be prevented. As described, according to the present embodiment it becomes possible to prevent the occurrence of poorly prepared examinations.

Figure 4:
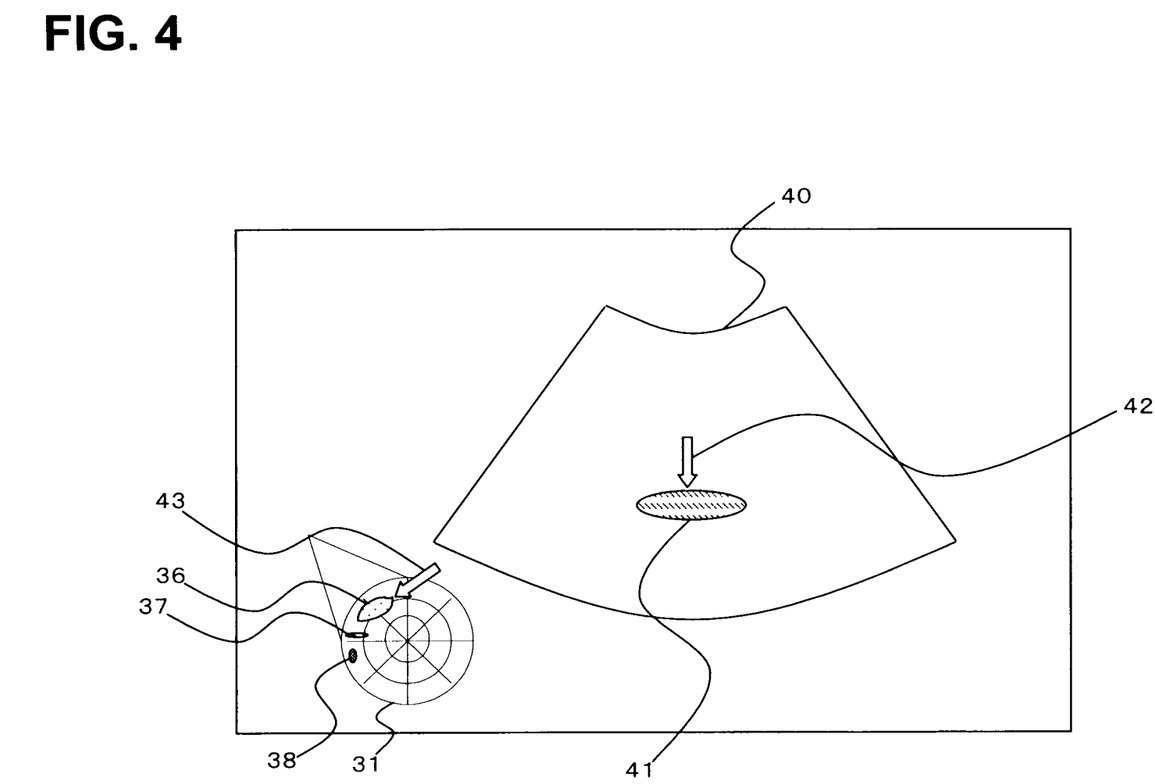
FIG. 4 illustrates a screen showing a tomographic image and a body mark in which a subjective symptom mark representing a subjective symptom has been set.

Herein, an example of a tomographic image generated by the image-generator 1 is shown in FIG. 4. FIG. 4 illustrates a screen representing a tomographic image and a body mark in which subjective symptom marks representing subjective symptoms have been set.

The controller 6 causes the display 12 to display the body mark 31 in which the subjective symptom marks 36, 37, 38 have been set. Once tomographic image data is generated by the image-generator 1, the controller 6 causes the display 12 to display a tomographic image 40 based on the tomographic image data.

When the operator (examiner) designates an area to be imaged on the body mark 31 using the operating part 13, the controller 6 then instructs to display a mark 43 representing the area to be imaged in the designated location. Furthermore, when the operator (examiner) designates a location that is equivalent to a causal area 41 of the subjective symptoms on the tomographic image 40 using the operating part 13, the controller 6 instructs to display a mark 42 in the designated location. In the example shown in FIG. 4, the marks 42, 43 each have an arrow-like shape. The arrow shape is merely an example, and other shapes may also be used.

The controller 6 links medical questionnaire information including subjective symptoms as well as location information indicating the locations of subjective symptoms in a body mark to the ultrasonic image data generated by the image-generator 1 and causes the storage 8 to store the same. In the example shown in the FIG. 4, the controller 6 links the subjective symptom marks 36, 37, 38, mark 43, as well as body mark 31 and tomographic image data in which the mark 42 has been set and causes the image-data-storage 8 to store the same.

Once the operator designates the desired ultrasonic data, the controller 6 then reads in the designated ultrasonic image data from the image-data-storage 8 and causes the display 12 to display an ultrasonic image based on the ultrasonic image data. Furthermore, the controller 6 reads in subjective symptom marks corresponding to the subjective symptoms that are included in the medical questionnaire information linked to the designated ultrasonic image data from the mark-storage 9. Then, the controller 6 causes the display 12 to display the same by overlapping the subjective symptom marks on the body mark.

Moreover, the controller 6 may also cause the image-data-storage 8 to store the ultrasonic image that is being displayed in the display 12, the body marks, and the subjective symptom marks as one image data. Once the operator selects desired image data, the controller 9 then reads in the designated image data from the image-data-storage 8 and causes the display 12 to display the ultrasonic image, body marks, and subjective symptom marks that are contained in the image data.

As described, by linking the ultrasonic image data and the medical questionnaire information, when a medical examiner (doctor) conducts a medical examination, once desired ultrasonic image data is designated, an ultrasonic image based on the ultrasonic image data and the medical questionnaire information linked to the ultrasonic image data are displayed in the display 12. Specifically, a body mark in which subjective symptom marks have been set is displayed in the display 12. When conducting a medical examination, the medical examiner (doctor) may conduct a medical examination by comparing a tomographic image and subjective symptom marks while taking the subjective symptoms into consideration. That is, the medical examination may be conducted by taking into consideration the link between the subjective symptoms declared by the subject to be examined and the tomographic image obtained by the examiner.

Because identification information such as a patient's ID has been attached to the tomographic image data, once the operator (doctor) enters the identification information using the operating part 13, the controller 6 obtains tomographic image data attached with the identification information from the image-data-storage 8. The controller 6 then causes the display 12 to display a tomographic image based on the tomographic image data. For example, once tomographic image data in which the mark 42 has been set, the controller 6 causes the display 12 to display a tomographic image 40 based on the tomographic image data. The mark 42 is then displayed in an overlapping manner on the tomographic image 40. Moreover, because the subjective symptom marks 36, 37, 38, mark 43, and body mark 31 have been linked to the tomographic image data, the controller 6 causes the display 12 to display the body mark 31 and to instruct to display the subjective symptom marks 36, 37, 38, and the mark 43 in an overlapping manner on the body mark 31. In the event of conducting a medical examination based on the tomographic image 40, the medical examiner (doctor) is able to conduct the medical examination by referring to, for example, the subjective symptom mark 36 while collating the tomographic image 40 and the subjective symptom.

The medical examiner (doctor) then conducts a medical examination while referring to the tomographic image 40 as well as the subjective symptom marks and enters the results of the medical examination using the operating part 13. Upon receiving the entry of the results of the medical examination from the operating part 13, the controller 6 causes the medical-examination-results-storage 10 to store the subjective symptoms and the results of the medical examination by linking the same. For example, the controller 6 links the results of the medical examination entered from the operating part 13 and the subjective symptom marks linked to the tomographic image 40 and causes the medical-examination-results-storage 10 to store the same. The subjective symptoms and the results of the medical examination are thus linked. The controller 6 may also classify the results of the medical examination for each subjective symptom and cause the medical-examination-results-storage 10 to store the same.

As described, by linking and saving subjective symptoms declared by the subject to be examined and the results of the medical examination by the medical examiner (doctor), it becomes possible to analyze the presence/absence of any links between subjective symptoms and example cases or the progress of illness.

Furthermore, other than using body marks or subjective symptom marks, the medical questionnaire information of a subject to be examined may also be represented by character information. For example, when the operator (examiner) enters medical questionnaire information of the subject to be examined as text information by using the operating part 13, the controller 9 causes the display 12 to display the medical questionnaire information through characters. Furthermore, once location information indicating the areas with the subjective symptoms declared by the subject to be examined is entered by the operator (examiner) as character information using the operating part 13, the controller 9 causes the display 12 to display the location information along with the medical questionnaire information. For example, if names indicating each region of a breast are preliminarily defined, the operator simply has to enter the name representing the declared area with a subjective symptom by using the operating part 13.

As described, by displaying medical questionnaire information and location information in the display 12, the examiner is able to conduct imaging with ultrasonic waves while checking the declared area that have subjective symptoms. It thus becomes possible to conduct imaging without missing any body part to be examined.

Moreover, the controller 6 links medical questionnaire information as well as location information to the ultrasonic image data generated by the image-generator 1 and causes the image-data-storage 8 to store the same.

Once the operator designates desired ultrasonic image data, the controller 6 then reads in the designated ultrasonic image data from the image-data-storage 8 and causes the display 12 to display an ultrasonic image based on the ultrasonic image data. Moreover, the controller 6 causes the display 12 to display the medical questionnaire information as well as location information that have been linked to the designated ultrasonic image data together with the ultrasonic image.

As described, by linking the medical questionnaire information as well as the location information to the ultrasonic image data, when conducting a medical examination, it becomes possible to conduct the medical examination while taking the link between subjective symptoms and an ultrasonic image into consideration.

Furthermore, the operator may also designate locations that are equivalent to the areas declared by the subject to be examined in body marks through the operating part 13 and may use their voice to enter medical questionnaire information including subjective symptoms. The controller 6 causes the display 12 to display a mark in the designated area of a body mark in an overlapping manner. In this case, the controller 6 links the location information indicating the designated locations in the body mark and the voice information representing the voice that has been entered and causes the image-data-storage 8 to store the same.

As described, by displaying a mark indicating the declared area with a subjective symptom in an overlapping manner on a body mark, the examiner is able to conduct imaging with ultrasonic waves while checking the declared area with the subjective symptom.

Moreover, the controller 6 links the location information of the designated location in a body mark as well as the voice information to the ultrasonic image data generated by the image-generator 1 and causes the image-data-storage 8 to store the same.

Once the operator designates desired ultrasonic image data, the controller 6 then reads in the designated ultrasonic image data from the image-data-storage 8 and causes the display 12 to display an ultrasonic image based on the ultrasonic image data. Furthermore, the controller 6 causes the display 12 to display a body mark and to display a mark in the location indicated by the location information that has been linked to the ultrasonic image data in an overlapping manner with the body mark. Once the operator uses the operating part 13 and designates a desired mark from the marks that are being displayed in an overlapping manner with the body mark, the controller 6 then replays the voice information that has been linked to the location where the mark is being displayed. The medical questionnaire information linked to the location where the mark is attached is thus replayed in the form of a voice.

As described, by linking medical questionnaire information as voice information to ultrasonic image data, when conducting a medical examination, it becomes possible to conduct the medical examination while taking the link between subjective symptoms and an ultrasonic image into consideration.

The display 12 comprises displays such as a liquid crystal display or a CRT.

The operating part 13 comprises a keyboard, a mouse, a trackball or TCS (Touch Command Screen), etc. An operator is able to designate a subjective symptom mark by using the operating part 13. The operator is able to designate a location in a body mark that is equivalent to an area with a subjective symptom declared by a subject to be examined by using the operating part 13.

The controller 6 is connected to each part of the image-generator 1 and conducts controlling of each part. In this embodiment, the controller 6 conducts controls such as: display control of ultrasonic image data, display control of subjective symptom marks, display control of body marks, linking between subjective symptoms and results of a medical examination, receipt of medical questionnaire information that has been entered from the operation part 13, and transmission/receipt control of ultrasonic waves through the transmitter/receiver 3. Furthermore, the controller 6 embodies one example of both the "receiver" and the "controller" in the present invention.

Moreover, the controller 6 comprises a storage such as a CPU (Central Processing Unit), a ROM (Read Only Memory), and/or a RAM (Random Access Memory). In the storage, an ultrasonic diagnosis support program has been stored for executing the functions of the ultrasonic diagnosis support system. When the CPU executes the ultrasonic diagnosis support program, a function to display ultrasonic image data, a function to display subjective symptom marks, a function to display body marks, a function to link subjective symptoms and results of a medical examination, and a function to receive medical questionnaire information that has been entered from the operating part 13 are each executed.

(Actions)

Figure 5:
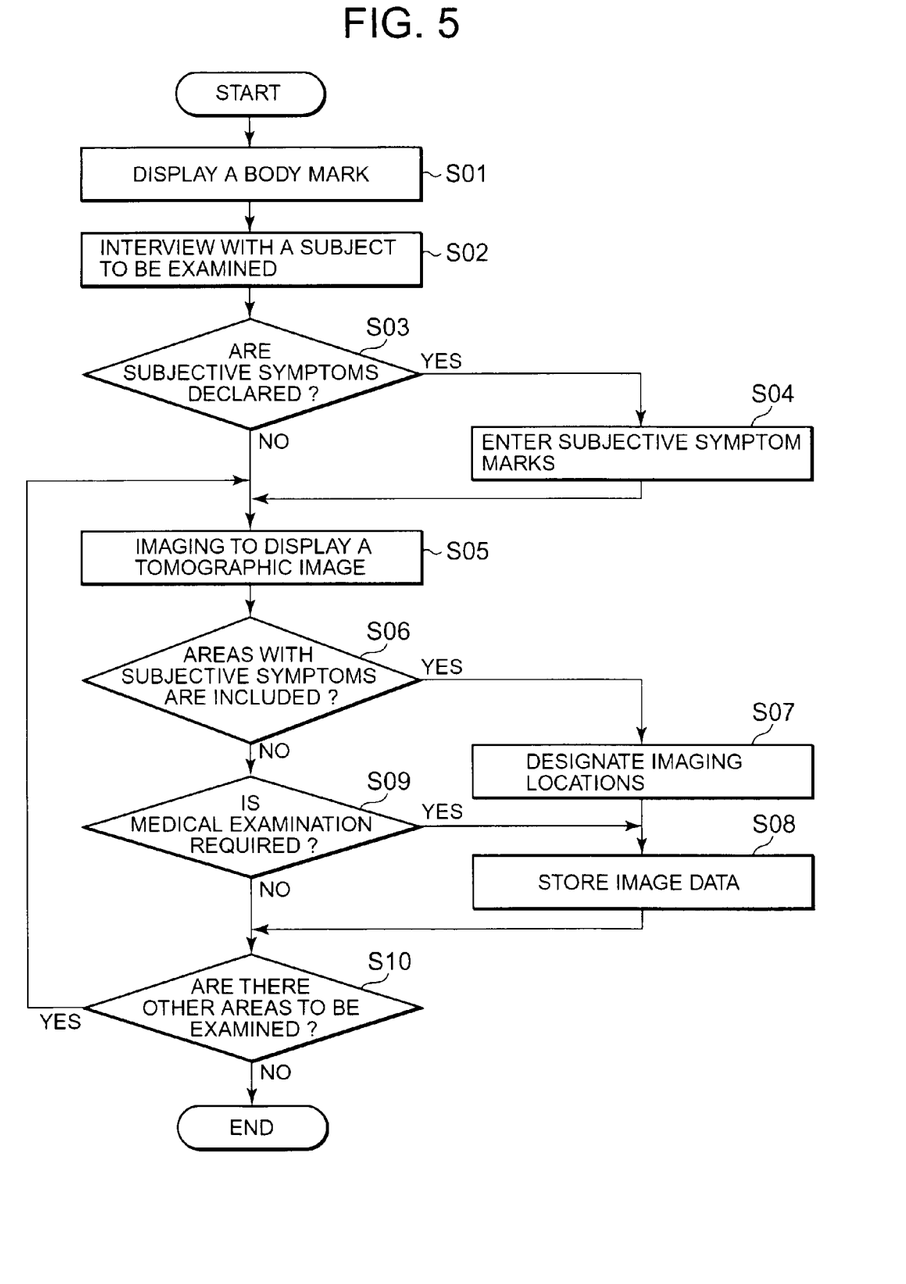
FIG. 5 is a flow chart for explaining a series of actions according to the ultrasonic diagnosis support system related to the embodiment of the present invention.

Next, a series of actions of an ultrasonic diagnosis support system related to the embodiment of the present invention is described with reference to FIG. 5. FIG. 5 is a flowchart for describing a series of actions conducted by the ultrasonic diagnosis support system related to the embodiment of the present invention.

(Step S01)

Before imaging with ultrasonic waves, the controller 6 causes the display 12 to display a body mark representing a body part for imaging. For example, the controller 6 creates a table listing a plurality of body marks and causes the display 12 to display the table list. When conducting a medical check of mammary glands, the examiner designates a body mark representing a breast by using the operating part 13 while referring to the table list that is being displayed in the display 12. The controller 6 causes the display 12 to display a body mark 31 or a body mark 32 that represents a breast by obtaining the body mark from the mark-storage 9 as shown in FIG. 2. Furthermore, the controller 6 causes the display 12 to display a table listing subjective symptom marks representing subjective symptoms.

(Step S02)

The examiner then conducts an interview with the subject to be examined.

(Step S03, Step S04)

In the interview, if the subject to be examined declares subjective symptoms (Step S03, Yes), the examiner uses the operating part 13 and selects subjective symptom marks representing the subjective symptoms declared by the subject to be examined. Furthermore, the operator designates locations in the body mark 31 that are equivalent to the areas with the subjective symptom declared by the subject to be examined by using the operating part 13. The controller 6 (e.g., as shown in FIG. 3) causes the display 12 to display the subjective symptom marks 36, 37, 38 in the designated locations of the body mark 31 in an overlapping manner.

(Step S05)

The examiner then conducts imaging with ultrasonic waves. The areas that are equivalent to the locations of the subjective symptom marks 36, 37, 38 are imaged while checking the locations that are being displayed in the body mark 31 by referring to the body mark 31 that is being displayed in the display 12. As described, by conducting imaging while checking the areas to be imaged by the subjective symptom marks, it becomes possible for the examiner to conduct imaging without missing any area with a subjective symptom that has been declared by the subject to be examined.

If the subject to be examined does not declare any subjective symptoms (Step S03, No), the examiner conducts imaging under prescribed imaging conditions (Step S05).

The image-generator 1 transmits ultrasonic waves to the subject to be examined and generates tomographic image data based on the received reflection. The controller 6 causes the display 12 to display a tomographic image based on the tomographic image data. For example, as shown in FIG. 4, the controller 6 causes the display 12 to display the body mark 31, subjective symptom marks 36, 37, 38, and further causes the display 12 to display the obtained tomographic image 40.

(Step S06 to Step S08)

The examiner then observes the tomographic image 40 and determines whether the declared areas with subjective symptoms are included in the tomographic image 40. If the examiner determines that the declared areas with the subjective symptom are included in the tomographic image 40 (Step S06, Yes), the locations that are equivalent to the areas to be imaged are designated on the body mark 31 by using the operating part 13. Furthermore, the operator uses the operating part 13 and designates the locations on the tomographic image 40 that are equivalent to the causal areas 41 of the subjective symptoms. The controller 6 receives each designation from the operating part 13 and displays the marks 42, 43 in the designated locations (Step S07).

Moreover, the controller 6 links the subjective symptom marks 36, 37, 38, the mark 43, and the body mark 31 to the tomographic image data in which the mark 42 has been set and causes the image-data-storage 8 to store the same (Step S08). That is, the controller 6 causes the image-data-storage 8 to store the medical questionnaire information by linking to the tomographic image data. The controller 6 also attaches identification information such as the patient's ID, to identify the subject being examined, to the tomographic image data. Furthermore, through a printing part (not illustrated), the controller 6 may also output the tomographic image 40 to which subjective symptom marks and the like have been linked.

The controller 6 may also cause the image-data-storage 8 to store, as one image data, the tomographic image data in which the mark 42 has been set, as well as the subjective symptom marks 36, 37, 38, the mark 43, and the mark 31.

On the other hand, if the examiner determines that the declared areas with the subjective symptom are not included in the tomographic image 40 (Step S06, No), the operator determines whether a medical examination by a medical examiner (doctor) is required or not for a later date (Step S09). When the operator determines that a medical examination is required for a later date (Step S09, Yes), the controller 6 links the body mark 31 in which the subjective symptom marks 36, 37, 38 have been set to the tomographic image data and causes the image-data-storage 8 to store the same (Step S08).

(Step S10)

If there are other areas to be examined (Step S10, Yes), the processes of Step S05 to Step S09 are then executed again. On the other hand, if there are no other areas to be examined (Step S10, No), the examination of the subject to be examined finishes.

When a medical examiner (doctor) conducts a medical examination on a later date, the medical examiner enters identification information such as the patient's ID by using the operating part 13. The controller 6 receives the identification information from the operating part 13 and reads in tomographic image data to which the identification information has been attached from the image-data-storage 8. The controller 6 then causes the display 12 to display a tomographic image based on the tomographic image data. For example, as shown in FIG. 4, the controller 6 causes the display 12 to display the tomographic image 40 based on designated tomographic image data. Because subjective symptom marks and the like have been linked to the tomographic image data, the controller 6 causes the display 12 to display the subjective symptom mark 36 and the like along with the tomographic image 40 as shown in FIG. 4.

It thus becomes possible for the medical examiner (doctor) to conduct medical examination while taking subjective symptoms into consideration by referring to the tomographic image 40 and the subjective symptom marks.

When the medical examiner (doctor) enters the results of the medical examination by using the operating part 13, the controller 6 receives the results of the medical examination from the operating part 13 and causes the medical-examination-results-storage 10 to store the results of the medical examination that have been entered and the subjective symptoms by linking them. The controller 6 may also store the results of the medical examination by classifying them for each subjective symptom.

As described, by linking subjective symptoms and the results of an interview, it becomes possible to analyze the presence/absence of any links between the subjective symptoms and example cases, or the progress of the illness.

What is claimed is:

1. An ultrasonic diagnosis support system, comprising:
   processing circuitry configured to
      receive multiple sets of medical questionnaire information, each set including information of a plurality of types of medical symptoms related to a subject, and designate locations indicated by each of said received multiple sets of medical questionnaire information, the locations being located in a body part of said subject, and to cause a display to display the information of the medical symptoms included in the medical questionnaire information and location information indicating said designated locations relative to each other; and
      a mark memory configured to store a plurality of types of symptom marks, each symptom mark being a different graphical symbol representing a different medical symptom, and a plurality of body marks, each body mark representing a body part, wherein
   the processing circuitry is further configured to
      acquire, from said mark memory, one body mark designated from among the body marks;
      cause said display to display said one body mark;
      obtain, from said mark memory, multiple symptom marks, each corresponding to information of one of the medical symptoms included in the medical questionnaire information;
      cause said display to display said obtained multiple symptom marks in said designated locations within said body mark in an overlapping manner; and
      cause said display to display said one body mark and the overlapped multiple symptom marks alongside an ultrasonic image, based on ultrasonic image data.

2. The ultrasonic diagnosis support system according to claim 1, wherein the processing circuitry is further configured to:
   acquire the plurality of body marks and the plurality of types of symptom marks from said mark memory;
   cause said display to display a table listing said plurality of body marks as well as a table listing said plurality of types of symptom marks;
   receive designation of the multiple symptom marks among said table of symptom marks; and
   cause said display to display said designated multiple symptom marks in said designated locations within said designated body mark in the overlapping manner.

3. The ultrasonic diagnosis support system according to claim 1, wherein said one body mark is a mark representing a breast.

4. The ultrasonic diagnosis support system according to claim 1, further comprising:
   an image-generator configured to transmit ultrasonic waves to said subject, and to generate the ultrasonic image data based on said reflected waves from the subject; and
   an image data memory,
   wherein the processing circuitry is further configured to link said multiple sets of medical questionnaire information as well as the location information indicating said designated locations to said generated ultrasonic image data and to cause said image data memory to store the same.

5. The ultrasonic diagnosis support system according to claim 4, wherein the processing circuitry is further configured to:
   receive designation of the ultrasonic image data;
   acquire said designated ultrasonic image data from said image data memory;
   cause said display to display the ultrasonic image based on said designated ultrasonic image data; and
   cause the display to display the multiple symptom marks corresponding to the information of the plurality of types of medical symptoms included in the medical questionnaire information that has been linked to said designated ultrasonic image data, together with said ultrasonic image in the overlapping manner with said linked locations within said one body mark.

6. The ultrasonic diagnosis support system according to claim 5, further comprising:
   a medical examination results memory, wherein the processing circuitry is further configured to:
   receive results of a medical examination of said subject based on said ultrasonic image displayed on said display;
   link said received results of the medical examination and said multiple sets of medical questionnaire information; and
   cause said medical examination results memory to store the same.

7. An ultrasonic imaging apparatus, comprising:
   a mark memory configured to store a plurality of types of symptom marks, each symptom mark being a different graphical symbol representing a different medical symptom, and a plurality of body marks, each body mark representing a body part of a subject;
   an image-generator configured to transmit ultrasonic waves to said subject and to generate ultrasonic image data based on reflected waves from said subject;
   processing circuitry configured to
      receive multiple sets of medical questionnaire information, each set including information of a plurality of types of medical symptoms related to said subject;
      acquire, from the mark memory, one body mark designated from among the body marks;
      cause said display to display said one body mark;
      acquire, from the mark memory, multiple symptom marks, each corresponding to information of one of the medical symptoms included in the medical questionnaire information;
      receive designation of multiple locations within said body mark; and
      cause said display to display said acquired multiple symptom marks in all overlapping manner in said designated locations within said body mark; and
   an image data memory configured to store said medical questionnaire information and location information indicating the multiple locations of said symptom marks in said one body mark by linking to said generated ultrasonic image data.

8. The ultrasonic imaging apparatus according to claim 7, wherein the processing circuitry is further configured to:
receive designation of the ultrasonic image data;
acquire said designated ultrasonic image data from said image data memory;
cause said display to display an ultrasonic image based on said designated ultrasonic image data; and
cause said display to display the symptom marks corresponding to the information of the plurality of types of medical symptoms included in the multiple sets of medical questionnaire information that has been linked to said designated ultrasonic image data, together with said ultrasonic image in the overlapping manner with said linked locations within said one body mark.

9. An ultrasonic diagnosis support method, comprising:
entering multiple sets of medical questionnaire information, each set including information of a plurality of types of medical symptoms related to a subject;
entering locations indicated by said received multiple sets of medical questionnaire information, the locations being located in a body part of said subject;
displaying said received multiple sets of medical questionnaire information as well as location information indicating said entered locations relative to each other;
storing, in a mark memory, a plurality of types of symptom marks, each symptom mark being a different graphical symbol representing a different medical symptom, and a plurality of body marks, each body mark representing a body part;
acquiring, from the mark memory, one body mark designated from among the body marks;
causing said display to display said one body mark;
obtaining, from the mark memory, multiple symptom marks, each corresponding to information of one of the medical symptoms included in the medical questionnaire information;
causing, by a processor, said display to display said obtained multiple symptom marks in said locations within said body mark in an overlapping manner; and
causing said display to display said one body mark and said overlapped multiple symptom marks alongside an ultrasonic image, based on ultrasonic image data.

10. The ultrasonic diagnosis support method according to claim 9, further comprising:
displaying a table listing the plurality of body marks as well as a table listing the plurality of types of symptom marks;
receiving designation of the multiple symptom marks among said table of symptom marks; and
displaying said designated multiple symptom marks in the overlapping manner with said designated locations within said designated body mark.

11. The ultrasonic diagnosis support method according to claim 9, further comprising:
transmitting ultrasonic waves to said subject;
generating the ultrasonic image data based on reflected waves from said subject; and
storing, in a non-transitory image data memory, said received multiple sets of medical questionnaire information as well as location information indicating the locations of said symptom marks in said body mark as linked to said generated ultrasonic image data.

12. The ultrasonic diagnosis support method according to claim 11, further comprising:
receiving designation of the ultrasonic image data;
acquiring said designated ultrasonic image data from said image data memory, to display the ultrasonic image based on said designated ultrasonic image data; and
displaying the multiple symptom marks corresponding to the information of the plurality of types of medical symptoms included in the multiple sets of medical questionnaire information that has been linked to said designated ultrasonic image data, together with said ultrasonic image in the overlapping manner with said linked locations within said one body mark.

13. The ultrasonic diagnosis support method according to claim 12, further comprising:
entering results of a medical examination of said subject based on said ultrasonic image that is displayed; and
storing in a medical examination results memory said received results of the medical examination as well as said multiple sets of medical questionnaire information as linked.

* * * * *